United States Patent [19]

Collins et al.

[11] Patent Number: 4,895,133

[45] Date of Patent: Jan. 23, 1990

[54] HEAT PACK FOR SURVIVAL IN COLD WATER

[75] Inventors: Michael H. Collins; Edward T. Provost, both of Chester, England

[73] Assignee: Shell Oil Company, Houston, Tex.

[21] Appl. No.: 914,699

[22] Filed: Oct. 2, 1986

[30] Foreign Application Priority Data

Oct. 4, 1985 [GB] United Kingdom ............... 8524543

[51] Int. Cl.⁴ ..................... A61F 7/00; F24J 1/00
[52] U.S. Cl. ..................... 126/204; 126/263
[58] Field of Search ............. 126/263, 204; 44/3 R, 44/3 A, 3 B; 62/4; 128/399, 403, 402, 400

[56] References Cited

U.S. PATENT DOCUMENTS

| | | | |
|---|---|---|---|
| 1,729,044 | 9/1929 | Kirk et al. ................. | 126/263 X |
| 2,018,367 | 10/1935 | Lackenbach ................. | 126/263 X |
| 2,352,951 | 7/1944 | Geria ................. | 126/263 |
| 2,556,893 | 6/1951 | Zwiebach et al. ................. | 126/263 X |
| 2,618,257 | 11/1952 | Berkman ................. | 126/204 |
| 2,621,648 | 12/1952 | Carfano et al. ................. | 126/263 |
| 3,233,604 | 2/1966 | Reed et al. ................. | 126/263 |
| 3,429,672 | 2/1969 | Young ................. | 126/263 X |
| 3,583,386 | 6/1971 | Slack ................. | 126/204 |
| 3,884,216 | 5/1975 | McCartney ................. | 126/204 |
| 4,119,082 | 10/1978 | Miyamori et al. ................. | 126/263 |
| 4,142,508 | 3/1979 | Watson ................. | 126/263 |

FOREIGN PATENT DOCUMENTS 2941116 4/1981 Fed. Rep. of Germany .

Primary Examiner—Randall L. Green
Attorney, Agent, or Firm—Mark K. Smith

[57] ABSTRACT

A heat pack for supplying thermal energy to the wearer on immersion in cold water comprises a capsule in which water can be admitted. The capsule contains a heat generating agent arranged in a tablet having such a shape that a reactive surface is created which allows the agent to react exothermally with the water at a controlled reaction rate.

15 Claims, 2 Drawing Sheets

HEAT PACK FOR SURVIVAL IN COLD WATER

BACKGROUND OF THE INVENTION

The invention relates to a life preserving heat pack for supplying thermal energy to the wearer upon immersion in cold water.

Sudden immersion in cold waters such as the North Sea poses a severe threat to human life. If the human body is immersed in cold water at near freezing temperature the cooling effect of the water may rapidly cause hypothermia and thus a drastically reduced blood circulation.

DESCRIPTION OF THE PRIOR ART

Contemporary approaches to this problem rely to a large extent on thermal insulation of the human body. In this respect "dry" immersion suits are known which prevent contact of water with the wearer's skin and garments designed on the "wet suit" principle, admitting some water to reach the skin but minimizing through-flow via the garment. It is also known in the art to provide for example diver suits and survival garments with an active heat source in order to counteract the cooling effect of the water. U.S. Pat. No. 3,884,216 discloses a heater system to supply heated fluid through a diver's suit using an electrochemical energy source which is shortcircuited to produce heat by the reaction of magnesium with seawater. U.S. Pat. No. 2,618,257 discloses an insulated life preserver garment comprising a shell in which a water activated heat generating means is arranged wherein the wearer may regulate the water supply to the heat generating means by opening or closing a valve, thereby regulating the amount of heat generated. West German Patent No. 2,941,116 discloses a survival garment containing at selected locations capsules with chemicals which react exothermally with each other and which may be brought in contact with each other by breaking a seal between the capsules. These previously known heat sources exhibit several disadvantages such as their bulky volume and difficulties encountered to activate the heat source and to subsequently regulate the amount of heat required.

SUMMARY OF THE INVENTION

The object of the invention is to provide a lightweight life preserving heat pack which can be combined with commonly used offshore clothing and which can be easily activated to generate heat in such a manner that, at least after the source has been activated, the heat output is regulated automatically without requiring manual control by the wearer.

A heat pack according to the present invention comprises a capsule in which water can be admitted, the capsule containing a heat generating agent arranged in a tablet having such a shape that a reactive surface is created which allows the agent to react exothermally with the water at a controlled reaction rate. In an attractive embodiment of the invention the tablet is substantially cylindrical and comprises magnesium chloride as a heat generating agent.

The heat pack according to the invention may be attached to a safety belt around the waist of the wearer, or be arranged in the wearer's clothing such as a body-warmer garment that can be worn under a rainproof suit.

BRIEF DESCRIPTION OF THE DRAWINGS

Other objects, advantages and novel features of the invention will become apparent from the following detailed description of the invention when considered in conjunction with the accompanying drawings, wherein.

DESCRIPTION OF THE PREFERRED EMBODIMENT

Figure 1:
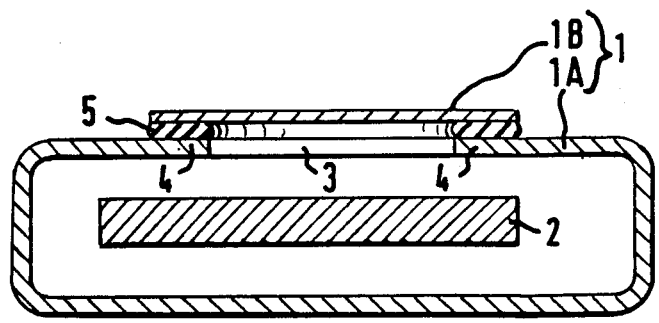
FIG. 1 is a cross-sectional view of a heat pack according to the invention illustrating an embodiment having a capsule consisting of two interbonded parts.

The heat pack shown in FIG. 1 comprises a capsule 1 containing a heat generating agent arranged in a tablet 2. The tablet 2 has a substantially cylindrical shape and the heat generating agent consists of magnesium chloride ($MgCl_2$). The magnesium chloride may be arranged in the tablet 2 either in the form of a solid block of anhydrous magnesium chloride or combined with a suitable binding agent.

The capsule 1 comprises two interbonded impermeable parts 1A and 1B. The first capsule part 1A has the shape of a flat box having an opening 3 in one of its sides. The second capsule part 1B is arranged as a patch covering the opening 3 in the first capsule part 1A and bonded to the rims 4 of the first capsule part 1A surrounding the opening 3 by means of a water soluble glue 5.

The capsule 1 consists of two interbonded impermeable parts which allows storage of the tablet 2 in a dry environment during normal conditions but which allows quick entry of water via the opening 3 into the capsule 1 upon immersion. After the water gets in contact with the tablet 2, exothermal hydration of the magnesium chloride at the surface of the tablet 2 starts. The rather small reactive surface-volume ratio of the tablet 2 enables the hydration to continue at a steady reaction rate so that a steady heat output during an hour or more may be achieved. For safety reasons it is essential that the hydration is tempered by creating a small reactive surface since otherwise a vigorous hydration of the magnesium chloride would take place resulting in a large heat output during a time interval of a few minutes only.

In general, controlling the hydration of magnesium chloride by only regulating the amount of water entering the capsule should be avoided since in emergency situations the wearer may be unable to adequately control the water inflow. Since the wearer may also be unable to activate the heat pack at the moment of immersion, it is preferred to use a water soluble glue 5 to interbond the capsule parts 1A and 1B so that the heat pack is activated automatically upon immersion. Dissolving of the water soluble glues by rainwater can be avoided by arranging the capsule in a garment inside an impermeable sack, which is turned upside down under normal conditions so that dripping rainwater does not reach the water soluble glue but which fills up with water upon immersion.

Figure 2:
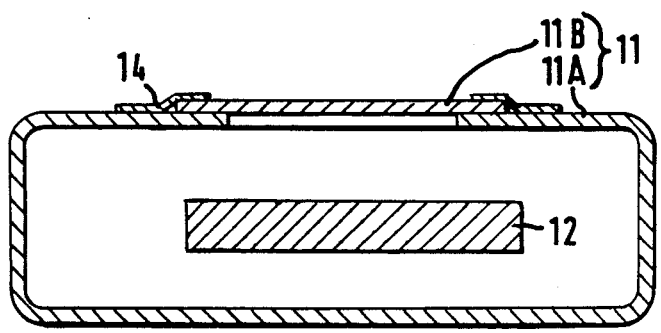
FIG. 2 is a cross-sectional view of a heat pack according to the present invention illustrating an embodiment having a capsule consisting of two parts which are interbonded by means of adhesive tape.

The heat pack shown in FIG. 2 comprises a capsule 11 consisting of two interbonded capsule parts 11A and 11B, which capsule 11 contains a magnesium chloride tablet 12 similar to the tablet described with reference to FIG. 1. In the heat pack of FIG. 2 however, the second capsule part 11B is bonded to the first capsule part 11A by means of a water soluble adhesive tape 14. The tape 14 consists of repulpable paper impregnated with glue means of a type known in the art. The large tape face area which is exposed to water upon immersion allows quick dissolution of the tape and thus quick activation of the heat pack.

Figure 3:
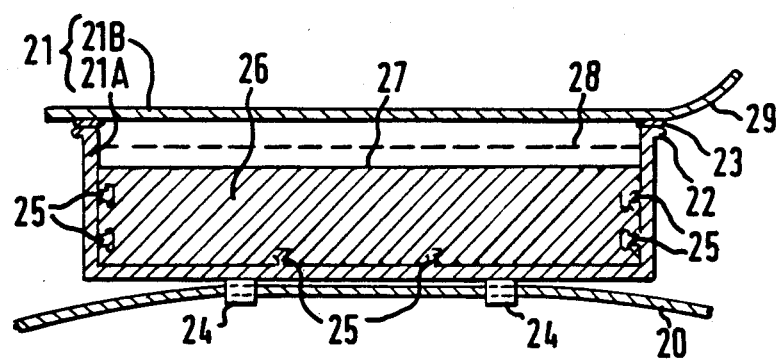
FIG. 3 is a cross-sectional view of a heat pack according to the present invention illustrating an embodiment attached to a safety belt.

FIG. 3 illustrates a heat pack comprising a capsule 21 which is connected to a safety belt 20 that can be secured around the waist of the wearer. The capsule 21 comprises an open box-like first part 21A and a flat second part 21B which is bonded to the terminal rims 22 of the first capsule part 21A by means of a water soluble glue 23. The first capsule part 21A consists of a rigid plastic shell which is provided at the outside thereof with a pair of molded-in belt loops 24 and at the inside thereof with a number of retaining ribs 25 for maintaining a magnesium chloride tablet 26 in a fixed position inside the capsule 21. The tablet 26 is molded in the first capsule part 21A in such a manner that water introduced after opening the capsule cannot enter between the tablet 26 and the walls of the first capsule part 21A so that hydration can take place only at the top side 27 of the tablet 26, whereas the remaining tablet surface is shielded-off. In this matter a small reactive surface is created and thus a moderated heat-flux is generated over a long interval of time, at least until a substantial part of the tablet has been hydrated. Further moderation of the reaction rate may be accomplished by arranging a flow stabilizing cover mesh 28 over the tablet 26 which mesh may, after opening the capsule, reduce flow pattern variations of the water entering the capsule and simultaneously provide reaction control by concentration effects.

As further illustrated in FIG. 3, the second capsule part 21B is provided with a pull tab 29 to enable manual activation of the heat pack immediately after immersion.

Figure 4A:
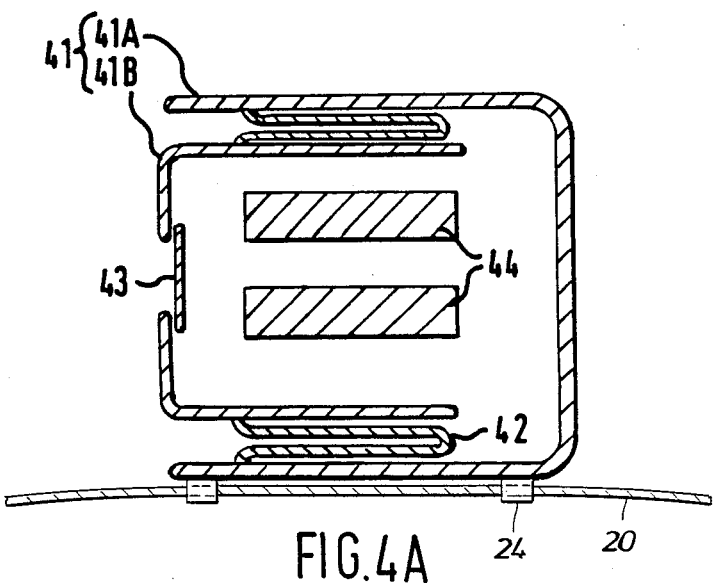
FIG. 4A is a cross-sectional view of a heat pack according to the present invention illustrating an embodiment having a capsule consisting of two telescoping parts.
Figure 4B:
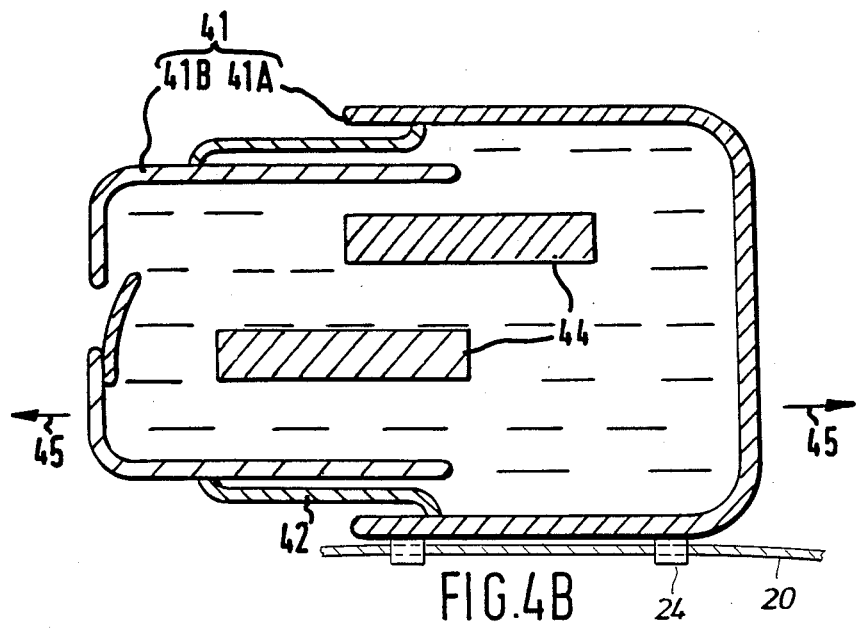
FIG. 4B is a cross-sectional view illustrating the heat pack of FIG. 4A after the two capsule parts have been telescoped away from each other.

FIGS. 4A and 4B illustrate another embodiment of the heat pack according to the invention. The heat pack shown in these figures comprises a capsule 41 comprising two telescoping cup-shaped parts 41A and 41B. The cup-shaped capsule parts 41A and 41B are sealingly interconnected by means of a flexible roll-sock membrane 42 which allows the capsule parts 41A, 41B to telescope from a compressed position shown in FIG. 4A towards an extended position shown in FIG. 4B while maintaining the seal provided by the membrane 42.

The second capsule part 41B is provided with a one-way flap valve 43 which allows water to be sucked into the capsule 41 in response to telescoping the capsule parts 41A, 41B towards the extended position thereof as shown by arrows 45 in FIG. 4B. Said ingress of water into the capsule 41 activates hydration of one or more magnesium chloride tablets 44 arranged in the capsule 41 thereby generating heat. Since the one way flap valve 43 does not allow escape of fluid from the capsule 41 a closed "hot bottle" is created and thus any contact of the products of said hydration with the wearer's skin is avoided.

The heat pack shown in FIG. 4 may be secured to a safety belt 20 like the heat pack of FIG. 3 and be provided with a pulling wire 46 to telescope the capsule parts away from one another, but if desired the heat pack may also be loosely stored inside a pocket of a life preserving garment and be activated after retrieving the heat pack from the pocket whereafter it is inserted at a location inside the garment where heat is needed. Alternatively, the heat pack may be built-in inside a body warmer garment which can be worn as a vest under rainproof clothing commonly used offshore.

If desired, the body warmer garment may further comprise flotation cells which fill up with gas automatically upon immersion as known in the art. The heat pack may be secured in such a manner to the garment that the telescoping capsule parts of the heat pack move automatically away from each other in response to inflation of said flotation cells, so that the heat pack is activated simultaneously with the flotation cells.

To produce the amount of heat required, a life preserving garment may be provided with a single heat pack which heats the layer of water between the garment and the wearer but, alternatively, the garment may be provided with a plurality of heat packs. In particular the "closed" heat pack illustrated in FIGS. 4A and 4B which acts as a hot water bottle may be used for protecting sensitive areas such as the hands and neck/occipital regions of the head by direct heat convection.

Reaction control is an important safety requirement under all circumstances and it has been found that the heat output/time profile of a heat pack can be successfully tailored to requirements by tabletting the heat generating agent to reduce the effective surface area where hydration takes place.

For tablets where anhydrous magnesium chloride is used along or with a suitable binding agent, such as the heat generating agent, it has been found that stable tablets can be formed with moderate compaction pressures during tabletting. The tablets thus formed had a compacted density of around 2000 kg/m$^3$: about twice the "loose powder" density of a magnesium chloride powder. Experiments have shown that a cylindrical tablet with a diameter identical to the height of the tablet and having a volume of about $7 \times 10^{-4}$m$^3$ containing 1.4 kg MgCl$_2$ with a typical density of about 2000 kg/m$^3$ is able to provide a power output of 300 W for 2 hours and thus a total heat production of 2 MJ. Although the amount of heat required to avoid hypothermia of the human body depends on various factors such as body size, water temperature and the presence of further passive thermal insulating provided by clothing, it has been found that under practical circumstances a heat output of 200 to 400 W is sufficient to counteract the cooling effect of water having a temperature between 0 and 10° C.

It is to be understood that the tablet or tablets used in the heat pack according to the invention may be cylindrical, cuboid, spherical or be of any other desired shape.

Many other variations and modifications may be made in the apparatus described above by those having experience in this technology without departing from the concept of the present invention. Accordingly, it should be clearly understood that the apparatus depicted in the accompanying drawings and referred to in the foregoing description are illustrative only and are not intended as limitations on the scope of the invention.

What is claimed is:

1. A heat pack for supplying thermal energy to a wearer on immersion in cold water, comprising:
   a capsule in which water can be admitted;
   a tablet of a heat generating agent in the capsule having such a shape that the reactive surface created allows the agent to react exothermally with the water at a controlled reaction rate; and
   a flow stabilizing cover mesh connected to the capsule and covering the tablet.

2. A heat pack for supplying thermal energy to a wearer on immersion in cold water, comprising:
   a capsule in which water can be admitted, said capsule comprising
   two substantially rigid telescoping parts which are interconnected by means of an impermeable membrane, one of said parts being provided with a water inlet valve, which allows inflow of water into the capsule in response to telescoping the capsule parts away from each other; and
   a tablet of a heat-generating agent in the capsule having such a shape that the reactive surface created allows the agent to react exothermally in the presence of a surplus of the water at a controlled reaction rate.

3. A heat pack in accordance with claim 2, wherein one capsule part is connected to a safety belt and the other capsule part is provided with a pulling wire for telescoping the capsule parts away from each other.

4. A heat pack for supplying thermal energy to a wearer on immersion in cold water, comprising:
   a capsule in which water can be admitted comprising:
   a plurality of substantially rigid telescoping parts;
   an impermeable membrane interconnecting the substantially rigid telescoping parts;
   a water inlet valve provided in at least one of the substantially rigid telescoping parts which allows inflow of water into the capsule in response to telescoping the capsule parts away from each other; and
   a tablet of a heat generating agent within the capsule having such a shape that a reactive surface is created which allows the agent to react exothermally with the water at a controlled rate.

5. A heat pack constructed in accordance with claim 4 wherein the tablet is substantially cylindrical in shape.

6. A heat pack constructed in accordance with claim 4 wherein the tablet consists of a solid block of anhydrous magnesium chloride.

7. A heat pack constructed in accordance with claim 4, further comprising:
   a safety belt connected to one of the substantially rigid capsule parts; and
   a pulling wire connected to another of the substantially rigid capsule parts;
   whereby tension applied to the pulling wire pulls the substantially rigid capsule parts away from each other.

8. A heat pack constructed in accordance with claim 4 wherein the heat generating agent comprises magnesium chloride.

9. A heat pack constructed in accordance with claim 8 wherein the tablet further comprises a binding agent.

10. A heat pack for supplying thermal energy to a wearer on immersion in cold water, comprising:
    a capsule in which water can be admitted, said capsule comprising:
    a plurality of impermeable parts;
    means for attaching the impermeable parts in a sealed, but removable, relation, wherein the means for attaching the impermeable parts is a water-soluble adhesive; and
    a tablet of a heat-generating agent in the capsule having a shape that the reactive surface created allows the agent to react exothermally in the presence of a surplus of the water at a controlled reaction rate.

11. A heat pack constructed in accordance with claim 10 wherein the water soluble adhesive consists of repulpable paper impregnated with glue.

12. A heat pack for supplying thermal energy to a wearer on immersion in cold water, comprising:
    a capsule in which water can be admitted, said capsule comprising:
    a plurality of impermeable parts;
    means for attaching the impermeable parts in a sealed, but removable, relation; and
    a tablet of a heat-generating agent in the capsule having a shape that the reactive surface created allows the agent to react exothermally in the presence of a surplus of the water at a controlled reaction rate; and
    a safety belt attached to the capsule.

13. A heat pack for supplying thermal energy to a wearer on immersion in cold water, comprising:
    a capsule in which water can be admitted, said capsule comprising two substantailly rigid telescoping parts which are interconnected by means of an impermeable membrane, one of said parts being provided with a water inlet valve, which allows inflow of water into the capsule in response to telescoping the capsule parts away from each other; and
    a tablet of a heat generating agent in the capsule having such a shape that the reactive surface created allows the agent to react exothermally with the water at a controlled reaction rate.

14. A heat pack in accordance with claim 13, wherein one capsule part is connected to safety belt and the other capsule part is provided with a pulling wire for telescoping the capsule parts away from each other.

15. A heat pack in accordance with claim 14 wherein the water inlet valve is unidirectional and does not permit the exit of water from the capsule.

* * * * *